United States Patent
Ghosh et al.

(10) Patent No.: US 7,666,234 B2
(45) Date of Patent: Feb. 23, 2010

(54) PROCESS FOR THE PREPARATION OF FATTY ACID METHYL ESTER FROM TRIGLYCERIDE OIL BY TRANSESTERIFICATION

(75) Inventors: Pushpito Kumar Ghosh, Gujarat (IN); Subbarayappa Adimurthy, Gujarat (IN); Mahesh Ramnikbhai Gandhi, Gujarat (IN); Nilesh Kumar Kanjibhai Vaghela, Gujarat (IN); Meena Rajnikant Rathod, Gujarat (IN); Bhupendra Dhanvantrai Shethia, Gujarat (IN); Jayant Batukrai Pandya, Gujarat (IN); Rajendra Amrutlal Parmar, Gujarat (IN); Prakash Jagjivanbhai Dodia, Gujarat (IN); Mehul Ghanshyambhai Patel, Gujarat (IN); Dahyabhai Revabhai Parmar, Gujarat (IN); Sanat Natwarlal Patel, Gujarat (IN)

(73) Assignee: Council of Scientific and Industrial Research (IN)

( * ) Notice: Subject to any disclaimer, the term of this patent is extended or adjusted under 35 U.S.C. 154(b) by 744 days.

(21) Appl. No.: 11/022,397

(22) Filed: Dec. 23, 2004

(65) Prior Publication Data

US 2006/0080891 A1   Apr. 20, 2006

(30) Foreign Application Priority Data

Oct. 20, 2004   (IN)   ............ 2056/DEL/2004

(51) Int. Cl.
*C11B 1/00* (2006.01)
*C11B 1/04* (2006.01)
*C10L 8/00* (2006.01)

(52) U.S. Cl. ............ 44/308; 554/8; 554/9; 554/30; 554/124; 554/156; 554/157; 554/174

(58) Field of Classification Search ............ 554/156, 554/157, 195, 174; 44/308
See application file for complete search history.

(56) References Cited

U.S. PATENT DOCUMENTS

| | | | |
|---|---|---|---|
| 6,399,800 B1 * | 6/2002 | Haas et al. | 554/156 |
| 2004/0102640 A1 * | 5/2004 | Brunner et al. | 554/174 |
| 2005/0065034 A1 * | 3/2005 | Miele et al. | 504/367 |

* cited by examiner

*Primary Examiner*—Ellen M McAvoy
*Assistant Examiner*—Chantel Graham
(74) *Attorney, Agent, or Firm*—Ostrolenk Faber LLP

(57) ABSTRACT

The present invention relates to an improved process for the preparation of biodiesel from triglyceride oils through transesterification, particularly the fatty acid methyl ester of oil mechanically expelled from whole seeds of *Jatropha curcas*, a plant with potential for cultivation on wastelands in India and other countries, all unit operations being carried out at ambient temperature.

22 Claims, No Drawings

PROCESS FOR THE PREPARATION OF FATTY ACID METHYL ESTER FROM TRIGLYCERIDE OIL BY TRANSESTERIFICATION

FIELD OF THE INVENTION

The present invention relates to an improved process for the preparation of biodiesel from triglyceride oils obtained from plant materials by transesterification. More specifically, the present invention relates to preparation of fatty acid methyl ester of oil expelled from whole seeds of *Jatropha curcas*, a plant that has potential for cultivation on wasteland in India and other countries.

BACKGROUND OF THE INVENTION

The depletion of fossil fuel and their polluting effect has spurred interest in renewable sources of energy, e.g., solar energy, wind energy, tidal energy, draught animal power, and energy that can be derived from plant sources.

Reference is made to a review article titled "*Biodiesel fuel production by transesterification of oils*" by H. Fukuda et al. (*Journal of Bioscience and Bioengineering*, vol. 92, No. 5, (2001), 405-416) that discusses the drawbacks of using vegetable oils directly in place of fossil diesel and the three approaches being investigated to overcome these drawbacks, namely, pyrolysis, micro-emulsification and transesterification. This article further states that transesterification is the preferred approach, and that such transesterification of oils can be effected by three routes, namely, acid catalysis, base catalysis and enzyme catalysis. While each route has its merits, base catalysis is the most industrially acceptable route presently in view of the much faster rate of reaction and inexpensive nature of the catalyst. The drawbacks of the current alkali-catalysed process as reported are: higher than ambient reaction temperature (60-70° C.), problems encountered with free fatty acid in the raw oil, difficulty encountered in recovering glycerol and methanol, and need for repeated washing of the methyl ester with water to effect its purification. No mention is made about the fate of the catalyst and the manner of effluent disposal.

Reference is made to the same review article above wherein it is stated that in a report entitled "*An overview of biodiesel and petroleum diesel life cycles*" by Sheehan et al. (Report of National Renewable Energy Laboratory (NREL) and US-Department of Energy (DOE) Task No. BF886002, May (1998)), it has been shown that the benefit of using biodiesel is proportionate to the level of blending with petroleum diesel. The overall life cycle emissions of $CO_2$ from 100% biodiesel fuel are 78.45% lower than those of petroleum diesel, and a blend with 20% biodiesel fuel reduces net $CO_2$ emissions by 15.66%.

Reference is made to the article entitled "*Biodiesel: A Renewable Energy Fuel*" by N. S. K. Prasad (Chemical Weekly, Aug. 17, 2004, p 183-188) wherein it is mentioned on p 186 that: "Biodiesel is widely used in Europe. Germany has more than 1500 filling stations selling biodiesel at the pump. France is the world's largest producer. All French Diesel fuel contains between 2-5% biodiesel that will soon apply to the whole of Europe. In the 1990s, France launched the local production of biodiesel fuel (known locally as diester) obtained by the transesterification of rape seed oil. It is mixed to the proportion of 5% into regular diesel fuel, and to the proportion of 30% into the diesel fuel used by captive fleets (public transportation). Renault, Peugeot and other manufacturers have certified truck engines for use with up to this partial biodiesel. Experiments with 50% biodiesel are underway."

Reference is made to a Google search: http://www.google.co.in/search?hl=en&q=Biodiesel+preparation&btnG=Google+Search&meta, that yielded 13,200 different results related to biodiesel preparation.

Reference is made to the paper entitled "*Integrated biodiesel production: a comparison of different homogeneous catalysts systems*" by Vicente et al. (*Bioresource Technology* 92 (2004) 297-305) wherein the process of transesterification of vegetable oils with different base catalysts is described. The authors report that the maximum yield of biodiesel obtained by them using alkali catalysed methanolysis is ca. 85.32% and 90.54% for NaOH and KOH-catalysed reactions, respectively, for laboratory scale experiments with oil having <0.5% FFA. Besides less than desirable yield, other drawbacks of the process are the need to carry out the transesterification reaction at higher than ambient conditions and the lack of any suitable solution to the problem of catalyst disposal and effluent management.

U.S. Pat. No. 6,489,496, describes a process for transesterification of triglycerides with continuous removal of glycerol produced during the reaction using centrifugal separator to enhance the reaction rate. The major draw back of the process is that the transesterification reaction is carried out at 70° C. The process does not describe the removal of catalyst from the glycerol, removal of methanol from the ester product, and recycling the excess ethanol; and hence the process is rendered uneconomical for industrial practice.

U.S. Pat. No. 6,712,867 discloses a process for production of fatty acid methyl esters from fatty acid triglycerides wherein the process of transesterification of triglycerides using methanol and/or ethanol, alkali catalyst and cosolvent like ether. The major drawbacks of the process are: (i) the use of cosolvent, higher than ambient transesterification temperature, and lack of any attempt to deal with the problem of spent catalyst discharge.

The Internet site http://www.svlele.com/biodiesel_in_india, discloses a detailed project report on Biodiesel manufacturing unit of 10 kl per day capacity. The project report is based on known prior art which, as mentioned above, has important limitations.

US Patent Application No. 20030229238 dated Dec. 11, 2003 relates to a continuous transesterification process, wherein the process includes a continuous, plug-flow environment with a single-pass residence time as low as about 10 seconds, and a conversion of at least 70 percent. The major draw back of the process is that it employs high temperature and pressure for transesterification reaction.

In another article W. Zhou et al, titled "Ethyl esters from the Single-Phase Base-Catalyzed Ethanolysis of Vegetable Oils" (JAOCS vol. 80, 367-371, 2003) the base catalyzed transesterification of vegetable oils has been carried out using cosolvent tetrahydrofuran (THF) and ethanol at elevated temperature. The draw backs of this publication are: the transesterification is carried out at elevated temperatures, and the use of additional solvent in the system renders the process complicated and expensive. Further, the article is silent on the recovery of the catalyst in any form and that of excess alcohol used in the reaction.

There are several literature reports wherein lipases have been used as catalysts in industrial processes for producing Biodiesel; for example Bradin (U.S. Pat. No. 6,398,707) uses a pretreated immobilized lipase to catalyze the transesterification or esterification. Further, the pretreated immobilized lipase is prepared by immersing an immobilized lipase in an alcohol having a carbon atom number not less than 3 and the pretreatment of lipase requires time up to 48 hours. Such processes are time consuming for industrial production. In another article published by Watanabe, et al., ["*Continuous Production of Biodiesel Fuel from Vegetable Oil Using Immobilized Candida antarctica Lipase*", *JAOCS*, vol. 77, pp. 355-360, 2000], there are three major difficulties in using lipase to produce Biodiesel. The first difficulty is that price of lipase is much higher than price of alkali. Secondly lipase process requires up to 48 hours to complete the reaction which is significantly longer than with base catalysis. The third difficulty is that the activity of lipase is relatively low, and it requires pretreatment with an alcohol having a carbon atom number not less than 3. Another difficulty with enzyme catalysis not alluded to in the article is that, for transesterification with methanol which is the preferred alcohol for biodiesel preparation, the reaction is extremely sluggish and proceeds in most cases with only low conversion efficiency, if at all.

Although ways of circumventing the problems associated with alkali-catalysed biodiesel preparation through use of alternative catalysts such as enzymes, acids and heterogeneous catalysts are described, it would be greatly beneficial if the base-catalysed process itself could be improved to overcome the current drawbacks. One such reported improvement is 2-stage transesterification but, here again, this slows down the overall throughput of the reaction and it would be desirable if high quality biodiesel, such as that conforming to EN14214 specifications, can be produced in a single stage. There are also no reports of any suitable means of overcoming the problem of messy work up of the crude fatty acid methyl ester obtained on transesterification of triglyceride with methanol, and losses of product/reagents in aqueous effluent. Moreover, given that biodiesel is about promoting green technology, it would be highly desirable if the entire process of producing such biodiesel from raw oil is carried out under ambient conditions. Another limitation of the prior art is that in attempting to maximize biodiesel yield, the process sometimes can be more complex than desirable and it would be of interest to have a simpler process where useful co-products are obtained along with biodiesel and, in the process, the overall method of production is maintained as simple as possible.

A Google search:
http://www.google.co.in/search?hl=en&q=Biodiesel+preparation+from+Jatropba+oil&btnG=Google+Search&meta provided 141 results related to biodiesel from *Jatropha curcas* oil. The oil obtained from the non-traditional *Jatropha curcas* plant is non-edible.

Reference is made to a book titled *Biofuels and Industrial Products from Jatropha curcas*, G. M. Gublitz, M. Mittelbach, M. Trabi, Eds. (1997), wherein it is reported by G. D. Sharma et al. that the *J. curcas* plant can be grown over a wide range of arid or semi-arid climatic conditions, is hardy to weather conditions, easy to propagate by seed or cuttings, and not browsed by goat or cattle. Reference is also be made to an article by B. Schmook and L. Serralta-Peraza in the same book wherein the authors state that "Taking into account the climatic and edaphic conditions of the Yucatan Peninsula, which are not very favorable for modern agriculture, *J. curcas* could be an option." It will be evident that the plant is suitable for cultivation on wasteland and large quantities of biodiesel may become available from wasteland in future if biodiesel of desired quality can be produced in simple and cost-effective manner. Reference is also be made to articles in the above book by E. Zamora et al. and M. N. Eisa on transesterification of *J. curcas* oil. The articles do not disclose much of the details of the process adopted. Reference is also made to the same book above wherein the utility of *Jatropha* oil cake, soap cake and glycerol have been reported in different chapters.

Reference is made to the Petroleum Conservation Research Association web site (http://www.pcra.org/petroleum16.html) wherein it is stated that triglycerides, including *Jatropha* oil, are "readily transesterified in the presence of alkaline catalyst (Lye) at atmospheric pressure and temperature of approximately 60-70° C. with an excess of methanol The mixture at the end of reaction is allowed to settle. The excess methanol is recovered by distillation and sent to a rectifying column for purification and recycled. The lower glycerol layer is drawn off while the upper methyl ester layer is washed with water to remove entrained glycerol Methyl esters of fatty acids are termed as bio-diesel." Apart from the fact that transesterification is conducted at higher than ambient temperature, no mention is made of the layer from which methanol is recovered or what is done with the alkali. There is also no mention of the complications expected to be encountered when water is added into the crude biodiesel layer.

The Minutes of Meeting of Adhoc Panel of experts of PCD 3 constituted by Bureau of Indian Standards for finalising Specifications of Biodiesel held on 17 Jun. 2004 which has been circulated for comments, wherein it is stated that: "On bio-diesel there are two important overseas standards, namely, EN 14214 and ASTM D 6751. The scope of EN 14214 covers the requirements of bio-diesel for its use as 100% and also for blending with diesel whereas the scope of ASTMD 6751 covers the requirements of bio-diesel only blend stocks." The report further states that: "Considering the fact that the bio-diesel in India is expected to be manufactured from non edible vegetable oils, members felt that it would be extremely difficult to meet the EN specifications."

Reference is made to an article by M. N. Eisa, titled "*Production of ethyl esters as diesel fuel substitutes in the developing countries*" (pp 110-112), in *Proceedings on Biofuels and Industrial Products from Jatropha curcas*, 23-27 Feb. 1997, held in Managua, Nicaragua. The article discloses the preparation of ethyl ester of oil by base catalyzed transesterification. The draw backs of this process are that they use large excess of ethyl alcohol (up to 70 parts per 100 parts of oil) and they did not recover the catalyst and the reaction temperature is also at around 70° C.

Reference is also be made to a publication by N. Foidl et al, titled "*Jatropha Curcas L as a Source For The Production of Biofuel in Nicaragua*" (*Bioresource Technology*, 58, 1996, pp 77-82) wherein it is stated that for developing countries like Nicaragua, *Jatropha curcas* is a very promising energy plant since the plant can be grown on very poor soils and gives a high average yield of seeds. The publication further describes the method of producing methyl ester of the oil, effectively by the 2-step base-catalysed transesterification process. The oil having 0.60-1.27% FFA is expelled from the seed kernel of *Jatropha curcas* seeds and then processed with 1.5 equivalents of MeOH and 1.3% KOH in a continuous reactor, with recycling of 90-93% of the methyl ester with fresh oil. The remaining ester phase is mixed with 5% of warm water and then centrifuged to eliminate excess methanol, remaining soaps and glycerol. The main disadvantages of the process are: (i) the need to decorticate the seeds, (ii) the low throughput because of high recycle ratio, and (iii) the high phosphorous (17.5 ppm) and moisture (0.16%) levels which would make the product unsuitable for use as neat biodiesel. No mention is also made of the complications of work up of the crude methyl ester, effluent management and the fate of the catalyst used.

Reference is made to the composition of the oil from *J. Curcas* seeds of Caboverde variety and Nicaragua variety reported in the above article. It is stated that the oil contains 290 ppm of phosphorous, and its level in biodiesel can be reduced to 17.5 ppm in the adopted process but degumming is necessary to produce biodiesel with <10 ppm of phosphorous as mandated in the EN14214 specifications for B100 biodiesel.

It will be evident from the prior art that there is no report wherein pure biodiesel of EN14214 specification has been prepared from *Jatropha curcas* oil, not to mention preparation of such premium quality biodiesel from oil expelled directly from whole seeds. Moreover, there is no report of biodiesel preparation under ambient conditions of processing which would minimize generation of greenhouse gases during processing. There is also little indication in the prior art of the economics of production and any attempts to value add effluents and flue gases. Lack of a suitable solution to the problem of spent alkali catalyst value addition, coupled with the cost of catalyst, may compel lower than optimum quantities of catalyst to be otherwise used that can adversely affect the process. There is also no report wherein the process has been optimized keeping the value of all products in mind.

Reference may be made to H. Scherzberg et al. who in their paper entitled 'Messo pilots new potassium sulphate process', (Phosphorous & Potassium, 178, March-April 1992, p-20) describe the utility of potassium sulphate as a superior fertilizer having both potassium and sulphur as plant nutrients and additionally having low chloride index.

Reference is made to an article on Potassium Compounds by H. Schultz et al. in Ullmann's Encyclopedia, 6$^{th}$ Edition, 2002, wherein the preparation of potassium carbonate from caustic potash and carbon dioxide is reported to be the most popular. It is further stated that: "the glass industry is the most important consumer of $K_2CO_3$. Large amounts are also required for potassium silicate manufacture." Besides many other applications, potassium carbonate is used as a fertilizer for acidic soil.

Reference is made to U.S. Pat. No. 6,174,501, by H. Noureddini discloses a system and process for producing biodiesel fuel with reduced viscosity and a cloud point below thirty-two (32) degrees Fahrenheit in which the utility of crude glycerol for preparation of glycerol ethers. These ethers are shown to lower the cloud point of the biodiesel obtained through based catalysed transesterification of triglycerides.

OBJECTS OF THE INVENTION

The main object of the invention is to provide an improved process for the preparation of fatty acid methyl ester (biodiesel) from triglyceride oil through transestrification Another object of the present invention is to provide an improved process for the preparation of biodiesel from triglyceride oil obtained from plant materials.

Another object of the present invention is to provide an improved process for the preparation of biodiesel of *Jatropha* oil that complies with EN14214 specifications and is suitable for use as biodiesel in neat form in mobile and stationary engines without any engine modification.

Another object of the present invention is to produce biodiesel under ambient conditions from raw oil expelled from whole seeds of *Jatropha curcas*.

Another object of the present invention is to produce biodiesel with least energy input and minimum effluent formation.

Another object of the present invention is to reduce the FFA content of oil to <0.5% by treating the raw oil under ambient conditions with required quantity of caustic soda solution of optimum concentration and to simultaneously eliminate pigments, phospholipids and other impurities in the raw oil along with the soap cake.

Another object of the present invention is to convert the soap cake containing 15-20% residual oil into a laundry bar.

Another object of the present invention is to sparge the neutralized oil with dry air to reduce the moisture content of the oil.

Another object of the present invention is to dry the methanolic-KOH used for transesterification of the oil with anhydrous sodium sulphate.

Another object of the present invention is to improve the method of work up of crude fatty acid methyl ester after tranesterification of the oil.

Another object of the present invention is to wash crude methyl ester after separation of glycerol layer with additional amounts of glycerol so as to extract out much of the methanol, catalyst and other impurities in methyl ester into the glycerol layer and thereby eliminate the problem of emulsion and froth formation, as also undesirable impurity-forming reactions, when the methyl ester is washed with water.

Another object of the present invention is to use water having <50 ppm total dissolved solids for washing the fatty acid methyl ester.

Another object is to add an antioxidant to the water-washed biodiesel and sparge with dry air to reduce the moisture content to <500 ppm.

Another object of the present invention is to take advantage of the improved process and work up procedure to produce biodiesel with 96% yield (w.r.t. neutralized oil) and ≦0.15% total glycerol through one-step transesterification of neutralized oil.

Another object of the present invention is to minimize COD and TDS of aqueous washings.

Another object of the present invention is to confine all of the KOH and excess methanol used in the reaction in the glycerol layers produced during reaction and used for washing of the crude fatty acid methyl ester.

Another object of the present invention is to treat the alkaline glycerol layer with $SO_x$ or concentrated sulphuric acid so as to convert the spent catalyst into solid fertilizer grade potassium sulphate that can be filtered and washed.

Another object of the present invention is to treat the alkaline glycerol layer with flue gases from the boiler in the biodiesel plant so as to convert the spent catalyst into potassium carbonate that can be filtered and washed.

Another object of the present invention is to distill the methanol in the glycerol layer for reuse after drying.

Another object of the present invention is to recycle a part of the crude glycerol remaining after methanol distillation for washing of crude methyl ester as described above.

Another object of the present invention is to utilize a part of the crude glycerol for preparation of glycerol ether to reduce the cloud point of the biodiesel as described in the prior art.

Another object of the present invention is to distill the balance amount of crude glycerol having low water content so as to produce refined glycerol cost-effectively.

Another object of the present invention is to provide a model of biodiesel production wherein biodiesel is produced in rural areas in the vicinity of the cultivation site and both the biodiesel as also by-products of the biodiesel process can be utilized locally to the maximum extent possible.

SUMMARY OF THE INVENTION

The aim of the present invention is to provide an improved process for the preparation of fatty acid methyl ester (biodiesel) from oil expelled mechanically from whole seeds of *Jatropha curcas*. Biodiesel is produced from raw oil under ambient conditions by first removing FFA and other impurities from the oil and thereafter using a single step KOH-catalysed transesterification followed by a novel work up based on initial washing of crude fatty acid methyl ester with glycerol followed by washing with water to remove traces of remaining impurities. The work up confines all the excess methanol and alkali in glycerol, which is then processed with greater cost-effectiveness and energy-efficiency to recover individual constituents (methanol, glycerol, potash) from the mixture. A further novelty is the use of flue gases in the above process. Biodiesel complying with EN14214 specification is obtained in >96% yield (w/w) w.r.t. neutralized oil and all by-products obtained are of commercial value. As a result of the above inventions, the effluent load is at a minimum.

Inventive Steps (1) The main inventive step is the recognition that improving the process of work up of the methyl ester of *Jatropha* oil after transesterification is the key to improving the overall process economics and biodiesel quality.

(2) Another inventive step is the recognition that, whereas methanol is poorly soluble in *Jatropha* oil, it is much more soluble in the methyl ester of *Jatropha* oil, i.e., in the biodiesel, and as a result considerable quantities of methanol and alkali catalyst used in the transesterification reaction, as also soaps, remain solubilised in the biodiesel at the end of the reaction.

(3) Another inventive step is the recognition that, whereas it is desirable to have methanol and catalyst solubilised in the biodiesel to allow the transesterification reaction to proceed to completion, their subsequent removal from biodiesel by washing with water poses the following difficulties: (i) the methyl ester gets partially hydrolysed in presence of water and alkali to produce a soap which can promote emulsification of biodiesel and water, necesssitating long period of standing to break the emulsion, (ii) the yield and quality of biodiesel can be adversely affected as a result, (iii) biodiesel can be lost in aqueous effluent if clear separation of the layers is not achieved, (iv) methanol consumption will increase since methanol that remains dissolved in biodiesel will be lost in the water, (v) a part of the alkali catalyst will be wasted in the aqueous effluent, and (vi) treatment of the alkaline aqueous effluent will be costly and problematic.

(4) Another inventive step is the recognition that retention of methanol, catalyst, and soaps in methyl ester will be higher when 2-step transesterification is carried out since the relative proportion of glycerol formed in the second step of transesterification tends to be less and, consequently, the pulling out of methanol, catalyst and soap is less effective. By contrast, the weight of glycerol layer separated is approximately the same as the weight of methanolic KOH used when an optimum amount of methanol and KOH is used in a single step transesterification, as a result of which there is little residual impurities that need to be removed from the fatty acid methyl ester layer.

(5) Another inventive step is use of additional glycerol—obtained through recovery of glycerol from previous batches of biodiesel production—to pull off residual methanol, catalyst and other impurities remaining in biodiesel at the end of transesterification reaction, such glycerol layer cleanly separating from the ester layer upon standing for short duration.

(6) Another inventive step is washing off any residual methanol, catalyst and free glycerol in the methyl ester with water without encountering any problem of ester hydrolysis and emulsion formation, resulting in a methyl ester layer (biodiesel) that can be cleanly separated and has FFA, methanol, alkali metal, total glycerol and free glycerol impurity levels well below those specified in the EN14214 specifications.

(7) Another inventive step is sparging water-washed biodiesel with dry nitrogen or air at ambient temperature to drive off moisture and achieve residual moisture level <500 ppm.

(8) Another inventive step is incorporation of an antioxidant into the biodiesel after water washing to minimise oxidative degradation while sparging with air and subsequently on storage of the product.

(9) Another inventive step is producing clear, golden yellow biodiesel from dark brown, turbid raw *Jatropha* oil under ambient condition by taking advantage of the neutralization step of FFA reduction wherein the majority of other impurities in oil such as pigments, phospholipids and insoluble matter are eliminated along with soap cake.

(10) Another inventive step is the near-quantitative recovery of spent KOH catalyst confined in the glycerol layer in the form of solid sulphate of potash fertilizer or potassium carbonate.

(11) Another inventive step is the cost-effective recovery of methanol and glycerol from glycerol layer by keeping moisture content of the layer to a bare minimum as produced stoichiometrically during the neutralization of KOH.

(12) Another inventive step is treating the saponified mass obtained on removal of free fatty acid from *Jatropha* oil with additional quantity of caustic lye to convert all trapped oil into soap, and further upgrading the soap, if desired, by incorporating by-product glycerol generated in the biodiesel process.

(13) Another inventive step is the processing of oil for biodiesel entirely under ambient condition and economizing on energy by confining heating operations only to the small volume of glycerol layer.

(14) Another inventive step is the minimization of aqueous effluent load by cleaning up the methyl ester with glycerol prior to water wash and also by reusing the second lot of washings in the first water wash of subsequent batch and also by utilizing a part of the first water wash for preparation of NaOH solution required for the oil neutralization and soap making steps.

DETAILED DESCRIPTION OF THE INVENTION

The present invention provides an improved process for the preparation of fatty acid methyl ester (biodiesel) of triglyceride oil that comprises: (i) expelling oil from whole seeds and keeping aside the cake for application as organic manure, (ii) neutralizing excess free fatty acid in the oil with alkali and separating the soap cake, (iii) adding an antioxidant and sparging the oil with dry air to reduce moisture content, (iv) treating the oil with appropriate quantity of methanolic-KOH solution that is dried with anhydrous sodium sulphate, (v) separating the glycerol layer formed during the reaction by known technique, (vi) treating the fatty acid methyl ester layer with glycerol in two lots to further reduce methanol, catalyst and other impurities in the fatty acid methyl ester layer, (vii) separating the glycerol layers by known technique, (viii) washing the fatty acid methyl ester layer thereafter with water in two lots to minimize impurities to desired level, (ix) separating the aqueous washings by known technique, (x) adding additional quantity of antioxidant to the fatty acid methyl ester and sparging with dry air to minimize moisture content, (xi) collecting the glycerol layers and treating with $SO_x$ or flue gas to convert the spent KOH catalyst into $K_2SO_4$ or $K_2CO_3$, respectively, (xii) adjusting the pH to desired level and distilling off the methanol in glycerol layer, (xiii) hot centrifuging the remaining mass to separate out potassium salt from glycerol, (xiv) washing the salt to remove adhering impurities, (xv) keeping aside required amount of the crude glycerol for washing of the fatty acid methyl ester layer of subsequent batch and also for other applications where crude glycerol is directly useful, and (xvi) distilling the remaining crude glycerol having low water content to produce refined, neat glycerol.

In an embodiment of the invention, triglyceride oil may be obtained from the plant materials and more particularly from *Jatropha curcas*.

In another embodiment of the invention, the yield of fatty acid methyl ester (biodiesel) is between 94-98% based on neutralized oil.

In another embodiment of the invention, the average yield of oil mechanically expelled from whole seeds of *Jatropha curcas* employed in the invention was 20-30% (w/w).

In another embodiment of the invention, the oil cake containing 5-10% oil is ground and made suitable for application as organic manure.

In another embodiment of the invention, the free fatty acid content of the freshly expelled oil was in the range of 1.5% to 10.0% (w/w).

In another embodiment of the invention, the oil was treated under ambient condition with 5 N caustic soda solution, the quantity of alkali used being 0.7-1.0 equivalents (w.r.t. FFA) depending on the initial FFA of the oil, so as to yield neutralized oil having FFA in the range of 0.25-0.35% (w/w).

In another embodiment of the invention, neutralization enables other impurities in raw oil such as phospholipids and coloring matter to be eliminated along with the soap cake to yield oil with improved color, clarity and flow which, in turn, yields biodiesel of golden yellow color and high clarity.

In another embodiment of the invention, soap cake containing 10-30% residual oil is treated with additional quantity of alkali and other laundry ingredients to produce a laundry bar having required quality.

In yet another embodiment of the invention the moisture content of neutralized oil is reduced from ca. 0.1% to ca. 0.01% by sparging with dry air after addition of a suitable antioxidant in 5-50 ppm concentration.

In another embodiment of the invention, methanolic KOH used for transesterification is treated with stoichiometric quantity (w.r.t. KOH) of anhydrous sodium sulphate to trap any water that may form from the reaction of the alkali with alcohol.

In an embodiment of the invention, the above moisture removal steps increase methyl ester yield by 1-5% and concomitantly reduce by-products which are difficult to deal with.

In yet another embodiment of the invention, the oil is transesterified with methanolic KOH in two stages, and preferably in a single stage using ca. 1.5-2 equivalents of methanol and 1.5-2% (w/w) KOH w.r.t. the neutralized oil used.

In yet another embodiment of the invention, the crude methyl ester layer after removal of glycerol layer is treated with 1-10% additional quantity of glycerol to mop up remaining impurities in the methyl ester layer and thereby prevent its run off in aqueous stream when the methyl ester layer is washed with two lots of water having <50 ppm TDS and, more importantly, to prevent the unwanted hydrolysis of ester.

In yet another embodiment of the invention, a part of the first lot of wash water that typically measures 0.5-1.0 liters per liter of biodiesel, and contains 25,000-35,000 ppm COD, is used in the preparation of caustic lye required for the neutralization step and also for laundry bar preparation from soap cake and the rest is treated before discharge.

In yet another embodiment of the invention, the second lot of wash water that has 500-2000 ppm COD is used for the first water wash in a subsequent batch.

In yet another embodiment of the invention, the resultant methyl ester is treated with 5-50 ppm of antioxidant and more particularly BHT and sparged with dry air to reduce moisture content to <500 ppm.

In yet another embodiment of the invention, the major part of the KOH catalyst is confined in the glycerol layer and can be treated with stoichiometric quantity of concentrated sulphuric acid or $SO_x$ fumes or flue gases to convert the spent catalyst into useful potassic fertilizer in 95-100% yield that can directly find application in villages.

In yet another embodiment of the invention, methanol is recovered in 70-95% yield from the glycerol layer through distillation.

In yet another embodiment of the invention, a part of the crude glycerol after removal of spent alkali catalyst and methanol is recycled for washing of crude methyl ester of subsequent batches.

In yet another embodiment of the invention, the remaining glycerol having minimum water content can be distilled to obtain neat, refined glycerol in 85-95% yield.

The following examples are given by way of illustrations and therefore should not be construed to limit the scope of the present invention.

EXAMPLE 1

395 kg of whole seeds of *Jatropha curcas* from Gujarat, India were fed into a mechanical expeller to obtain 100 kg of dark brown oil and 282 kg of oil cake. Free fatty acid content (FFA) of freshly expelled oil was 4.42% (w/w). Out of this, 4.27 kg of oil was taken in a 10 L glass vessel equipped with an agitator (200 rpm). 155 ml of 5 N NaOH (1.16 mol equivalent) solution was added under stirring at room temperature over 15 min. Stirring was continued for 60 min and the saponified mass was vacuum filtered to obtain 0.68 kg of soap cake and 3.58 kg of clear, light brown oil (83.8% yield) with 0.30% (w/w) residual FFA.

EXAMPLE 2

1187 kg of a separate lot of *Jatropha curcas* seeds from Rajasthan, India were fed into the mechanical expeller of Example 1 to obtain 270 kg of dark yellow color oil having 3.2% (w/w) FFA. Out of this, 123.8 kg of oil was taken in a 200 L SS vessel equipped with a paddle agitator (100 rpm) and 2.58 L of 5N NaOH (0.92 mole equivalent) solution was added into the oil under stirring at room temperature over 10 min. Stirring was continued for 40 min and the saponified mass was filtered using high speed centrifuge to obtained 9.76 kg of cake and 115.8 kg of light yellow color oil (93.53% yield) having 0.26% (w/w) residual FFA.

EXAMPLE 3

194 kg of a separate lot of *Jatropha* seeds were mechanically expelled after the monsoon period to obtain 46 kg of turbid, black color oil having 7.87% FFA (w/w) oil and 134 kg of oil cake. Out of this, 1.75 kg of oil was taken in a 3 L glass vessel equipped with an agitator (200 rpm) and 95 ml of 5 N NaOH (0.97mol equivalent) solution was added under stirring at room temperature over 10 min. Stirring was continued for 30 min and the saponified mass was vacuum filtered to obtain 0.40 kg of soap cake and 1.43 kg of clear, dark brown oil (81.7% yield) having 0.267% (w/w) residual FFA.

Examples 1-3 teach us that raw oil expelled from whole seeds of *Jatropha curcas* have varying appearance and FFA but the process of neutralization can significantly upgrade the appearance besides reducing FFA to desired level. The Examples also teach us that optimum amount of alkali solution must be employed to minimize loss of oil in soap while ensuring at the same time required reduction in FFA content of the neutralized oil.

EXAMPLE 4

2.67 kg of the neutralized oil of Example 1 was transesterified in a three necked 5-liter capacity glass vessel with anchor type agitator. 0.530 kg of methanolic KOH solution was prepared in a separate vessel by adding 0.045 kg (1.68% (w/w) w.r.t. neutralized oil) of KOH into 0.485 kg MeOH (1.64 mol equivalent w.r.t neutralized oil) under stirring for 15 min. 0.372 kg of this solution was added into the oil under stirring at 200 rpm over 30 min at room temperature. The contents were further stirred for 1.00 h under ambient conditions. Agitation was then discontinued and the contents allowed to stand for 1 h, following which glycerol layer was taken from bottom of vessel and weighed 0.36 kg. 100 g aliquot of oil/methyl ester layer was taken for analysis and remaining amount was further transesterified with balance amount (0.158 kg) of methanolic KOH. 0.06 kg of glycerol layer was separated after discontinuing stirring and allowing the content to stand for 1 h. 2.54 kg of crude fatty acid methyl ester was obtained which was further processed by the following method:

0.25 kg of crude methyl ester was taken and the experiment of Method C above was repeated except that the 0.039 Kg of glycerol was added in two lots of 0.032 kg and 0.007 kg, respectively. After addition of the first lot and standing time of 10 min, 0.035 kg of glycerol layer was obtained, whereas 0.012 kg was obtained in the second case after standing for 1.5 h, i.e., a total of 0.052 kg. Compressed air was passed through silica gel and the resultant dry air was used to sparge the methyl ester layer for 45 min. 0.235 kg of product was obtained having 0.27% FFA, 0.05% total glycerol, <0.01% free glycerol, 0.048% moisture and <0.2 ppm each of sodium and potassium. The aqueous effluent (0.534 kg) contained 0.0089 g of KOH and its COD value was 7100 ppm.

EXAMPLE 5

(Comparative Methods A,B,C)

2.67 kg of the neutralized oil of Example 1 was transesterified in a three necked 5-liter capacity glass vessel with anchor type agitator. 0.530 kg of methanolic KOH solution was prepared in a separate vessel by adding 0.045 kg (1.68% (w/w) w.r.t. neutralized oil) of KOH into 0.485 kg MeOH (1.64 mol equivalent w.r.t neutralized oil) under stirring for 15 min. 0.372 kg of this solution was added into the oil under stirring at 200 rpm over 30 min at room temperature and the contents further stirred for 1.00 h under ambient conditions. Agitation was then discontinued and the contents allowed to stand for 1 h, following which the glycerol layer was taken from the bottom of the vessel and weighed 0.36 kg. A 100 g aliquot of the oil/methyl ester layer was taken for analysis and the remaining amount was further transesterified with the balance amount (0.158 kg) of methanolic KOH. 0.06 kg of glycerol layer was separated after discontinuing stirring and allowing the content to stand for 1 h. 2.54 kg of crude fatty acid methyl ester was obtained which was further processed by the methods (A-C) below:

Method A. 0.25 kg of the crude methyl ester was taken in a separatory funnel and shaken with 0.175 kg of water. A foamy emulsion was obtained which separated into two distinct but hazy layers after ca. 24 h. The aqueous layer was removed and 0.175 kg of water once again added into the separatory funnel to repeat the procedure. This time around 20 h was required to obtain the distinct layers. This procedure was continued for an additional six times with water having TDS <50 ppm, after which clear methyl ester was obtained. The methyl ester was filtered through a bed of anhydrous sodium sulphate to obtain of 0.205 kg of final product having 0.41% FFA, 0.05%, total glycerol, and 0.01% free glycerol. 1.45 kg of effluent water was obtained from the water wash having 0.395 g KOH and 43,500 ppm COD.

Method B. 0.25 kg of crude methyl ester was taken in a distillation flask and heated to a temperature of 65-75° C. to distill off residual methanol under vacuum. The mass turned jelly like and could not be processed further.

Method C. 0.25 kg of crude methyl ester was taken in a separatory funnel and treated with 0.039 kg of glycerol under stirring for one minute and allowed to stand for 90 min. The glycerol and methyl ester layers separated out into two clear, distinct layers. The weight of the separated glycerol layer was found to increase to 0.048 kg. 0.175 kg of water was then added into the methyl ester layer, the contents shaken and then allowed to stand for 2.5 h. The water layer separated easily. Subsequently, the methyl ester layer was subjected to two additional washes (0.175 kg×2) with water (<50 ppm TDS). The methyl ester layer was found to contain 0.2% moisture and was filtered through a bed of anhydrous sodium sulphate to obtain 0.235 kg of final product having 0.27% FFA, 0.05% total glycerol, <0.01% free glycerol, 0.1% moisture and 12 ppm of sodium impurity. The aqueous effluent (0.530 kg) contained 0.029 g KOH and its COD was 21800 ppm.

The above methods of work up in Examples 4-5 teach us that treatment of crude methyl ester with glycerol prior to water wash results in significant improvements in terms of increased yield, retention of the FFA value of neutralized oil, and significant reduction in effluent volume and COD. Additionally, the examples teach us that addition of glycerol in two lots has a more beneficial effect in terms of further reduction in effluent load. The examples also teach us that sparging of the purified methyl ester with dry air is the best method of reducing moisture level under ambient temperature. (The moisture level was found to be 600 ppm when purified methyl ester was dried in a rotavap at 70° C.)

EXAMPLE 6

500 kg of whole seeds of *Jatropha curcas* were fed into the mechanical expeller to yield 125 kg of dark brown oil containing 3.2% (w/w) FFA. Out of this, 105 kg (3.86 mol) of the oil was taken in a 200 L SS vessel equipped with a paddle agitator (100 rpm) and 2.7 L of 5N NaOH (13.5 mol) solution (1.16 mol equivalent of FFA) was added into the oil under stirring at room temperature over 10 min. Stirring was continued for 45 min and the saponified mass was filtered using a vacuum Nutsche filter to obtain 13.0 kg of cake and 92.5 kg of oil containing 0.26% (w/w) residual FFA. 18.3 kg of methanolic KOH solution was prepared in a separate vessel by adding 1.5 kg of KOH into 16.8 kg (1.64 mol equivalent w.r.t neutralized oil) MeOH under stirring for 15 min. This solution was added into the oil under stirring over 20 min at room temperature using a metering pump and the contents further stirred for 1 h under ambient conditions. Agitation was then discontinued and the contents allowed to stand for 1 h, following which the glycerol layer was taken from the bottom of the vessel and weighed 17.7 kg. The ester layer was again transesterified with an additional quantity of methanolic KOH prepared as above from 5.85 kg of MeOH (0.57 mol equivalent w.r.t neutralized oil) and 0.5 kg of KOH. No additional glycerol was separated. The biodiesel/ester layer was then treated with 12.6 kg of glycerol under stirring for one minute and allowed to stand for 90 min to ensure complete separation of the glycerol and biodiesel layers. The weight of the separated glycerol layer was 20.2 kg. The ester layer/biodiesel was subjected to three (90 L each) water washes, following which 0.9 g of BHT antioxidant was added. At this point, the moisture level in the biodiesel was 0.18% (1800 ppm) as estimated by Karl Fischer technique. Compressed air was passed through silica gel and the resultant dry air was used to sparge the biodiesel for 3 h. The biodiesel weighed 90 kg (97.3% yield w.r.t. neutralized oil). The biodiesel was analysed and found to contain 0.262% FFA, 0.048% total glycerol, 0.009% free glycerol and 450 ppm moisture. A sample from this batch was sent for detailed analysis and the results obtained are shown in the table below:

Analysis of Fatty Acid Methyl Ester of Example 3[a]

| | Appearance | | Clear, golden yellow liquid | |
|---|---|---|---|---|
| | | | DIN value | Actual value |
| Density @ 15° C. | ISO 3675 | kg/m$^3$ | 860-900 | 880.0 |
| solid contamination | | mg/kg | <24 | 4 |
| Neutralization Number | DIN 51 558-1 | mg KOH/g | <0.5 | 0.1 |
| Viscosity at 40° C. | ISO 3104 | mm$^2$/s | 3.5-5.0 | 4.34 |
| Iodine number | DIN 53241-1- | gJ$_2$/100 g | <120 | 96 |
| Ash | ISO 3987 | g/100 g | <0.02 | <0.01 |
| Water content | EN ISO 12937 | mg/kg | <500 | 450 |
| Flash point | DIN EN 22719 | ° C. | >101 | 160 |
| Cetane number[b] | — | | >51 | 54.5 |
| Gross Calorific Value[b] | D4809 | Kcal/kg | | 9562 |
| Monoglyceride | EN 14 105 | g/100 g | <0.8 | 0.15 |
| Diglyceride | EN 14 105 | g/100 g | <0.2 | <0.02 |
| Triglyceride | EN 14 105 | g/100 g | <0.2 | <0.02 |
| Free glycerine | EN 14 105 | g/100 g | <0.2 | <0.02 |
| Total glycerine | EN 14 105 | g/100 g | <0.25 | 0.04 |
| Methanol | prEN 14110 | g/100 g | <0.2 | <0.02 |
| Ester-content | prEN 14103 | g/100 g | — | 98.5 |

-continued

Analysis of Fatty Acid Methyl Ester of Example 3[a]

| | Appearance | | Clear, golden yellow liquid | |
|---|---|---|---|---|
| | | | DIN value | Actual value |
| Sodium | | mg/kg | <0.5 total | 0.2 |
| Potassium | | mg/kg | Na + Ka | 0.2 |
| Magnesium | | mg/kg | — | <0.5 |
| Calcium | | mg/kg | — | <0.5 |
| Phosphorus | | mg/kg | <10 | <1 |

[a]Analysis courtesy DaimlerChrysler AG, Germany
[b]Analysis courtesy Reliance Industries Ltd., India It can be seen from this example that fatty acid methyl ester of oil expelled from whole seeds of *Jatropha curcas* can be processed by the method of the invention with 2.2 eqv of methanol and 2.2% (w/w) KOH to obtain B100 biodiesel in 97.2% yield, wherein all parameters comply with EN 14214 specifications and most parameters are much below the specified limits. It can also be seen that the important limitation of the prior art vis-á-vis P content of biodiesel is overcome in the present invention.

EXAMPLE 7

115.8 kg of neutralized oil containing 0.26% (w/w) residual FFA was taken in a 200 L SS vessel equipped with a 100 rpm paddle-type agitator. 15.5 kg of methanolic KOH solution was prepared in a separate vessel by adding 1.305 kg of KOH into 14.2 kg MeOH (1.12 mol equivalent w.r.t neutralized oil) under stirring for 15 min. This solution was added into the oil under stirring over 30 min at room temperature using a metering pump and the contents further stirred for 1 h under ambient conditions. Agitation was then discontinued and the contents allowed to stand for 1 h, following which the glycerol layer was taken from the bottom of the vessel and weighed 17.28 kg. The ester layer was again transesterified with an additional quantity of methanolic KOH prepared as above from 6.24 kg of MeOH (0.5 mol equivalent w.r.t neutralized oil) and 0.56 kg of KOH. 4.58 kg additional glycerol was separated. The biodiesel/ester layer was then treated with 7.44 kg of glycerol under stirring for five minute and allowed to stand for 90 min to ensure complete separation of the glycerol and biodiesel layers. The weight of the separated glycerol layer was 11.3 kg. The ester layer/biodiesel was subjected to three RO water (<50 ppm TDS) washes (3×70 L), following which 1.1 g of BHT antioxidant was added. Compressed air was passed through silica gel and the resultant dry air was used to sparge the biodiesel for 3 h, following, which the moisture level reduced to 460 ppm. The biodiesel weighed 109.4 kg (94.5% yield w.r.t. neutralized oil) and contained 0.25% FFA, 0.11% total glycerol and 0.02% free glycerol.

EXAMPLE 8

80.1 kg of oil containing 0.36% (w/w) residual FFA was taken in a reactor. 14.46 kg of methanolic KOH solution was prepared in a separate vessel by adding 1.2 kg of KOH into 13.26 kg MeOH (1.5 mol equivalent w.r.t neutralized oil) under stirring for 15 min. This solution was added into the oil under stirring over 30 min at room temperature using a metering pump and the contents further stirred for 1 h under ambient conditions. Agitation was then discontinued and the contents allowed to stand for 1 h, following which the glycerol layer was taken from the bottom of the vessel and weighed 14.2 kg. The ester layer was again transesterified with an additional quantity of methanolic KOH prepared as above from 6.24 kg of MeOH (0.70 mol equivalent w.r.t neutralized oil) and 0.5 kg of KOH. 3.2 kg additional glycerol was separated. The biodiesel/ester layer was then treated with 10.2 kg of glycerol under stirring for five minute and allowed to stand for 90 min to ensure complete separation of the glycerol and biodiesel layers. The weight of the separated glycerol layer was 18.5 kg. The ester layer/biodiesel was subjected to three RO water (<50 ppm TDS) washes (3×70 L), following which 0.80 g of BHT antioxidant was added. Compressed air was passed through silica gel and the resultant dry air was used to sparge the biodiesel for 3 h, following, which the moisture level reduced to 0.048% (480 ppm). The biodiesel weighed 76.2 kg and its volume was 87 L. The biodiesel contained 0.36% FFA. Total glycerol and free glycerol were below detection limits.

Examples 5-7 teach that biodiesel complying with EN14214 specifications can be achieved when transesterification is carried out in two steps with total methanol and KOH amounts in the range of 1.62-2.20 eqv. and 1.6%-2.2%, respectively. As in the case of Example 4 (methods C and D), the FFA content of biodiesel is the same as that of neutralized oil. There is, however, a marginal drop of yield at the lower usage levels of methanol and catalyst. The examples also teach us that when the methanol and KOH amounts employed in the first stage are >1.62 eqv. and 1.6%, there is no observable amount of glycerol layer in the second stage of transesterification. This suggests that a single stage transesterification with optimum amounts of methanol and KOH to yield EN14214 grade biodiesel is feasible.

EXAMPLE 9

83 kg of neutralized *Jatropha* oil having 0.31% (w/w) residual FFA was taken in a reactor. 17.45 kg of methanolic KOH solution was prepared in a separate vessel by adding 1.45 kg KOH into 16.0 kg MeOH (1.74 mol equivalent w.r.t oil) under stirring for 15 min. This solution was added into the oil under stirring over 30 min at room temperature using a metering pump and the contents further stirred for 1.25 h under ambient conditions. Agitation was then discontinued and the contents allowed to stand for 1 h, following which the glycerol layer was taken from the bottom of the vessel and weighed 17.4 kg. A 250 mL aliquot from the methyl ester layer was taken and shaken with water in a separatory funnel. Clear separation of the layers was found to be difficult. The remaining methyl ester layer was treated with 6.35 kg of glycerol under stirring for one minute and allowed to stand for 90 min to ensure complete separation of the glycerol and ester layers. Weight of the separated glycerol layer was 7.55 kg. The ester layer was subjected to three washes with water (3×70 L) having <50 ppm TDS. 0.8 g of BHT antioxidant was then added into the methyl ester and the contents sparged with dry air for 3 h. The biodiesel, weighing 78 kg (94.0% yield w/w), contained 0.31% FFA, 0.15% total glycerol, <0.01% free glycerol and 450 ppm moisture.

EXAMPLE 10

105 kg of oil expelled from *Jatropha Curcas* seeds obtained from Udaipur, Rajasthan containing 1.67% (w/w) FFA was taken in a 200 L SS vessel equipped with a paddle agitator (100 rpm) and 1 L of 5N NaOH solution(0.82 mole equivalent of FFA) was added into the oil under stirring at room temperature over 15 min. Stirring was continued for 60 min and the saponified mass was filtered using centrifuge to obtain 4.5 kg of cake and 102.2 kg of oil containing 0.33% (w/w) residual FFA. 21.2 kg of methanolic KOH solution was prepared in a separate vessel by adding 1.78 kg of KOH into 19.4 kg MeOH (1.74 mol equivalent w.r.t neutralized oil) under stirring for 15 min. This solution was added into the oil under stirring over 30 min at room temperature using a metering pump and the contents further stirred for 1.25 h under ambient conditions. Agitation was then discontinued and the contents allowed to stand for 1 h, following which the glycerol layer was taken from the bottom of the vessel and weighed 22.84 kg. The crude ester layer was washed with glycerol in three splits of 1.08 kg, 1 kg and 1.06 kg respectively under stirring for five minute and allowed to stand for 60 min to ensure complete separation of the glycerol and biodiesel layers. The weight of the separated glycerol layers were 2.44 kg, 1.24 kg, and 1.28 kg, respectively. The methyl ester layer was washed with three lots of water (3×70 L) having <50 ppm. The COD values of the three successive water washes were 30400 ppm, 754 ppm and 257 ppm, respectively. 1 g of BHT antioxidant was added and dry air was used to sparge the methyl ester. The product, weighing 96.1 kg (94.1% yield w.r.t. neutralized oil), was found to contain 0.32% FFA, 0.156% total glycerol, 0.01% free glycerol and 480 ppm moisture.

EXAMPLE 11

527 kg of *Jatropha Curcas* seeds from Udaipur area of Rajasthan, India were subjected to crushing to obtain 125 kg of oil containing 1.78% (w/w) FFA. Out of this, 106 kg of oil was taken in a 200 L SS vessel equipped with a paddle agitator (100 rpm) and 1.1 L of 5N NaOH solution(0.82 mole equivalent of FFA) was added into the oil under stirring at room temperature over 15 min. Stirring was continued for 60 min and the saponified mass was filtered using a centrifuge to obtain 5.15 kg of cake and 102 kg of oil containing 0.31% (w/w) residual FFA. The neutralized oil exhibited moisture content of 0.1%. 1.2 gm of BHT was added into it and sparged with dry air for 30 minutes to reduce the moisture content to 0.025%. Methanolic KOH solution was prepared in a separate vessel by adding 1.81 kg of KOH (1.77% w.r.t. neutralized oil) into 19.7 kg MeOH (1.75 eqv of neutralized oil) under stirring for 15 min, and treated with 1 kg of anhydrous sodium sulphate. The resultant solution weighing 21.2 kg was added into the oil under stirring over 30 min at room temperature using a metering pump and the contents further stirred for 1.25 h under ambient conditions. Agitation was then discontinued and the contents allowed to stand for 1 h, following which the glycerol layer was taken from the bottom of the vessel and weighed 21.15 kg. The methyl ester layer was then washed with glycerol in three lots of 1.15 kg, 1.00 kg and 1.00 kg, respectively, under stirring for five minute and allowed to stand for 60 min to ensure complete separation of the glycerol and methyl ester layers. The weights of the separated glycerol layers were 2.06 kg, 1.55 kg, and 1.05 kg respectively. The methyl ester layer was then subjected to two washes (2×70 L) with water having <50 ppm TDS, following which 1 g of BHT antioxidant was added and the product dried by sparging with dry air. The biodiesel, weighing 98.05 kg (96.13% yield w.r.t. neutralized oil), was found to contain 0.31% FFA, 0.16% total glycerol, 0.01% free glycerol, and 450 ppm moisture.

Examples 8-10 teach that B100 biodiesel with total glycerol content ≦0.16% can be obtained in a single step transesterification with 1.74 eqv of methanol and 1.74% of KOH. The examples further teach that given that the weight of glycerol layer obtained is virtually the same as the weight of methanolic KOH taken for transesterification, there is little residual methanol and catalyst in the crude methyl ester, as a result of which even lower quantity of added glycerol suffices to pull off the impurities from the methyl ester layer. Additionally, Example 10 teaches that by removing moisture from neutralized oil and treating methanolic KOH with anhydrous sodium sulphate prior to transesterification, it is possible to reduce the impurity matter in glycerol layer and concomitantly increase the yield of fatty acid methyl ester from ca. 94% to 96%.

EXAMPLE 12

The separated glycerol layers of Example 7 were mixed together and 2 kg out of the total quantity of 35.9 kg, containing 58 g of potassium hydroxide (catalyst), was taken in a 5 L round bottom flask immersed in a trough containing cold water, and treated with 50 gm of 98% sulfuric acid (36M $H_2SO_4$) while ensuring that the temperature did not exceed 30° C. The mixture was stirred for about 15 min. The solid crystals were separated by filtration, washed with 400 gm of methanol and dried at 100° C. for one hour to obtain 78.7 gm (yield 88.4%) of potassium sulphate ($K_2O$ content=51.8%) suitable for application as potassic fertilizer. 1.88 kg of methanol—glycerol filtrate was charged into distillation assembly. 328 gm of methanol and 1.563 kg glycerol were obtained by the distillation.

EXAMPLE 13

37 kg of the separated glycerol layer produced during production of biodiesel in Example 5, containing 1.69 Kg of potassium hydroxide (catalyst), was taken in 50 L vessel, and treated with 1.315 kg of 98% sulfuric acid (36M $H_2SO_4$) at room temperature. The mixture was stirred for about 5 min and solid crystals separated by filtration, washed with 4.5 kg of methanol and dried at 100° C. for one hour to obtain 2.48 kg (94.4% yield w.r.t. KOH) of potassium sulphate ($K_2O$ content=47.3%) suitable for application as potassic fertilizer.

EXAMPLE 14

2.5 liters of glycerol layer obtained during biodiesel production from a batch was analysed and found to contain 101.3 g KOH spent catalyst. It was subjected to neutralization by bubbling $SO_3$. The mass was filtered, washed and dried to obtain 147.2 gm of potassium sulphate (93.5% yield).

EXAMPLE 15

1.43 kg of neutralized oil containing 0.267% (w/w) residual FFA was processed further for transesterification in three necked 3-liter capacity glass vessel with anchor type agitator. 198.1 gm of methanolic KOH solution was prepared in a separate vessel by adding 16.6 g of KOH into 181.5 g MeOH (1.15 mol equivalent w.r.t neutralized oil) under stirring for 15 min. This solution was added into the oil under stirring at 200 rpm over 20 min at room temperature and the contents further stirred for 1.00 h under ambient conditions. Agitation was then discontinued and the contents allowed to stand for 1 h, following which the glycerol layer was taken from the bottom of the vessel and weighed 207.5 gm. Extract was further transesterified for 1 h with methanolic KOH prepared from 75.5 gm of MeOH (0.5 mol equivalent w.r.t neutralized oil) and 7.0 gm of KOH as above. 80.2 gm of glycerol layer was separated after discontinuing stirring and allowing the content to stand for 1 h. Crude methyl ester was taken in a separatory funnel and treated with glycerol in two lots 100 gm and 41.9 gm respectively under stirring for one minute. After addition of the first lot and standing time of 10 min, 110.4 gm of glycerol layer was obtained, whereas 75.6 gm was obtained in the second case after standing for 1.5 h, i.e., a total of 186.3 gm. The ester layer/biodiesel was subjected to three RO water (<50 ppm TDS) washes (3×1L). Compressed air was passed through silica gel and the resultant dry air was used to sparge the biodiesel for 1 h, following which the moisture level reduced to 0.046% (460 ppm). The biodiesel weighed 1.35 kg and its volume was 1.54 L.

The total quantity of 465.3 gm of the separated glycerol layer produced during the production of Biodiesel was estimated to contain 3.79% (w/w) of potassium hydroxide (catalyst). It was taken in 2 L vessel, and treated with 15.3 gm of 98% sulfuric acid (36M $H_2SO_4$) at room temperature. The mixture was stirred for about 15 min. The solid crystals were separated by filtration, washed with 300 gm of methanol and dried at 100° C. for one hour to obtain 23.92 gm (87.3% yield w.r.t. KOH and 91.6% yield w.r.t. $H_2SO_4$) of potassium sulphate ($K_2O$ content=51.1%) suitable for application as potassic fertilizer. The filtrate containing methanol and glycerol was subjected to the vacuum distillation to recover 69 gm methanol (at 40° C. and 570 mmHg pressure) and 250.9 gm glycerol (at 250° C. and 570 mmHg). The overall recovery of methanol is 73% and that of glycerol is 86%.

Examples 11-14 show the method of recovering the spent catalyst in useful form and simultaneously recovering methanol and neat glycerol in energy efficient manner.

EXAMPLE 16

20 kg of soap cake, containing approximately 20% (w/w) oil, was obtained from the neutralization of *Jatropha* oil of different batches. It was taken in a jacketed vessel equipped with stirrer. 5 L of 10N NaOH solution was added into it under stirring in 10 minutes and heated up to 70° C.-80° C. The resultant slurry was poured into the tray and allowed to cool to room temperature. The soap exhibited fine soap properties and is suitable as laundry bar.

EXAMPLE 17

"Merc to run on pure biodiesel" by A. S. Anand (Times News Network, Apr. 5, 2004) refers to an intention to run an automobile using neat biodiesel. The biodiesel referred to is the one produced herein using the processes of Examples 5-10. "*Between Merc & Farmers, Comes Biodiesel*" published in The Financial Express of Apr. 22, 2004 (New Delhi Edition) reports on successful test running of a vehicle using ca. 800 L of the pure biodiesel obtained herein.

EXAMPLE 18

550 L of neat biodiesel produced as per the processes of Examples 5-10 was evaluated in a Powrin brand 8 HP stationary engine having the following specifications: bore, 114.3 mm; stroke, 139.7 mm; cubic capacity, 1.4330 L; nominal compression ratio 19:1; rpm, 850. The engine was run over ten 16 h cycles. The engine could be operated smoothly with the biodiesel without any modification.

Advantages of the Present Invention are:
i. The invention allows biodiesel of desired specification to be obtained from *Jatropha* oil expelled directly from whole seeds, even with one-step transesterification, without need for any elaborate purification.
ii. The process eliminates the need to subject *Jatropha* oil and biodiesel to heating or cooling and is advantageous from the viewpoint of energy efficiency and product quality.
iii. The invention involves simple unit operations and the yield of biodiesel obtained by the process of the invention is >96%.

iv. The process is environmentally friendly with low effluent discharge and recovery of useful by-products.

We claim:

1. A process comprising:
   (i) Treating a plant material to expel an oil therefrom while obtaining a cake of residual plant material;
   (ii) Treating the expelled oil with an alkali to neutralize excess free fatty acid in the expelled oil and separating a soap cake so formed;
   (iii) adding an antioxidant to the treated oil and sparging the treated oil with alkali, and separating out soap cake;
   (iv) treating the sparged oil with an appropriate quantity of methanolic-KOH solution dried with anhydrous sodium sulphate to obtain a glycerol layer and a fatty acid methyl ester layer;
   (v) separating the glycerol layer formed during the treatment in step (iv);
   (vi) treating the fatty acid methyl ester layer with glycerol in two lots to further reduce methanol, catalyst and other impurities in the fatty acid methyl ester layer;
   (vii) separating the glycerol layers obtained in step (vi);
   (viii) washing the fatty acid methyl ester layer obtained in step (vi) with water in two lots to reduce impurities;
   (ix) separating the aqueous washings;
   (x) adding an additional quantity of antioxidant to the fatty acid methyl ester and sparging with dry air to reduce moisture content, to obtain the fatty acid methyl ester;
   (xi) collecting the glycerol layers and treating the collected layers with $SO_x$ or flue gas to convert spent KOH catalyst therein into $K_2SO_4$ or $K_2CO_3$, respectively;
   (xii) adjusting pH and distilling off methanol contained in the glycerol layers;
   (xiii) hot centrifuging a remaining mass to separate out potassium salt from the glycerol;
   (xiv) washing said salt to substantially remove adhering impurities therefrom; and
   (xv) keeping aside a required amount of crude glycerol for washing a fatty acid methyl ester layer of a subsequent batch, and optionally also keeping aside a further required amount of the crude glycerol, and distilling the remaining crude glycerol having a low water content to produce therefrom refined, neat glycerol.

2. A process as claimed in claim 1 wherein the oil is obtained from *Jatropha curcas*.

3. A process as claimed in claim 1 wherein the yield of biodiesel is between 94-98% and meets EN14214 specification of biodiesel.

4. A process as claimed in claim 2 wherein average yield of oil mechanically expelled from whole seeds of *Jatropha curcas* is in the range of 20-30% (w/w).

5. A process as claimed in claim 1 wherein the oil cake contains 5-10% oil.

6. A process as claimed in claim 1 wherein free fatty acid content of the freshly expelled oil is in the range of 1.5% to 10.0% (w/w).

7. A process as claimed in claim 1 wherein in step (ii) the oil is treated under ambient condition with 5 N caustic soda solution, the quantity of alkali used being 0.7-1.0 equivalents with respect to the initial free fatty acid content of the oil, so as to yield neutralized oil having a free fatty acid content in the range of 0.25-0.35% (w/w).

8. A process as claimed in claim 1 wherein phospholipids and other impurities and coloring matter in the oil are removed by the neutralization in step (ii).

9. A process as claimed in claim 1 wherein the soap cake contains 10-30% residual oil and is treated with an additional quantity of alkali to produce a laundry bar.

10. A process as claimed in claim 1 wherein moisture content of neutralized oil is reduced from 0.1% to 0.01% by sparging with dry air after addition of a suitable antioxidant in a 30-50 ppm concentration.

11. A process as claimed in claim 1 wherein methanolic KOH used for transesterification in step (iv) is treated with stoichiometric quantity with respect to KOH of anhydrous sodium sulphate to trap any water formed from reaction of the alkali with alcohol.

12. A process as claimed in claim 1 wherein the moisture removed from neutralized oil and methanolic KOH increases methyl ester yield by 1-5% and concomitantly reduces by-products.

13. A process as claimed in claim 1 wherein the oil is transesterified with methanolic KOH in two stages, and in a single stage using ca. 1.5-2 equivalents of methanol and 1.5-2% (w/w) of alkali with respect to the neutralized oil used.

14. A process as claimed in claim 1 wherein the crude methyl ester layer remaining after removal of glycerol layer is treated with a 1-10% additional quantity of glycerol to mop up remaining impurities in the methyl ester layer, thereby preventing its run off in an aqueous stream when the methyl ester layer is washed with two lots of water having >50 ppm total dissolved salts, while also preventing unwanted hydrolysis of the ester.

15. A process as claimed in claim 1 wherein a part of the first lot of wash water from step (viii) that measures 0.5-1.0 liters per liter of biodiesel, and contains 25,000-35,000 ppm chemical oxygen demand is converted to caustic lye for use in neutralization of a laundry bar preparation from the soap cake, whereas the rest is treated before discharge.

16. A process as claimed in claim 1 wherein a part of the first lot of wash water in an amount of 0.5-1.0 liters per liter of biodiesel, and containing 25,000 -35,000 ppm Chemical Oxygen Demand is converted to caustic lye for use in laundry bar preparation formed from soap cake.

17. A process as claimed in claim 1 wherein the second lot of wash water out of two washes from step (viii) that has 500-2000 ppm chemical oxygen demand is used for the first water wash in a subsequent batch.

18. A process as claimed in claim 1 wherein in step (x) the resultant methyl ester is treated with 5-50 ppm of antioxidant comprising BHT and then sparged with dry air to reduce moisture content to >500 ppm.

19. A process as claimed in claim 1 wherein a substantial portion of the KOH catalyst is confined in the glycerol layer and is treated with a stoichiometric quantity of concentrated sulphuric acid or $SO_x$ fumes or flue gases to convert the spent catalyst into potassic fertilizer in 95-100% yield for direct application.

20. A process as claimed in claim 1 wherein methanol is recovered in 70-90% yield from the glycerol layer through distillation.

21. A process as claimed in claim 1 wherein a part of the crude glycerol after removal of spent alkali catalyst and methanol is recycled for washing of the crude methyl ester of a subsequent batch.

22. A process as claimed in claim 1 wherein remaining glycerol having minimum water content is distilled to obtain neat, refined glycerol in 85-95% yield.

* * * * *